(12) United States Patent
Carrel

(10) Patent No.: US 11,911,600 B2
(45) Date of Patent: Feb. 27, 2024

(54) INJECTION DEVICE FOR INJECTING A COMPOSITION CONTAINED IN A MEDICAL CONTAINER

(71) Applicant: Becton Dickinson France, Le Pont de Claix (FR)

(72) Inventor: Franck Carrel, Le Pont de Claix (FR)

(73) Assignee: Becton Dickinson France, Le Pont de Claix (FR)

( * ) Notice: Subject to any disclaimer, the term of this patent is extended or adjusted under 35 U.S.C. 154(b) by 881 days.

(21) Appl. No.: 16/966,396

(22) PCT Filed: Jan. 31, 2019

(86) PCT No.: PCT/EP2019/052393
§ 371 (c)(1),
(2) Date: Jul. 30, 2020

(87) PCT Pub. No.: WO2019/149826
PCT Pub. Date: Aug. 8, 2019

(65) Prior Publication Data
US 2020/0360618 A1    Nov. 19, 2020

(30) Foreign Application Priority Data

Feb. 2, 2018  (EP) .................................... 18305109

(51) Int. Cl.
*A61M 5/315*    (2006.01)
*A61M 5/20*     (2006.01)
*A61M 5/24*     (2006.01)

(52) U.S. Cl.
CPC ...... *A61M 5/31571* (2013.01); *A61M 5/2033* (2013.01); *A61M 5/3158* (2013.01);
(Continued)

(58) Field of Classification Search
CPC ............ A61M 5/31571; A61M 5/2033; A61M 5/3158; A61M 2005/2073;
(Continued)

(56) References Cited

U.S. PATENT DOCUMENTS

| 2006/0069350 A1 | 3/2006 | Buenger et al. |
| 2013/0035634 A1 | 2/2013 | Cappello et al. |
| 2017/0224928 A1* | 8/2017 | Högdahl ............. A61M 5/3204 |

FOREIGN PATENT DOCUMENTS

| JP | 2000116772 A | 4/2004 |
| JP | 2012511353 A | 5/2012 |
| WO | 2010066706 A1 | 6/2010 |

* cited by examiner

*Primary Examiner* — Jason E Flick
(74) *Attorney, Agent, or Firm* — The Webb Law Firm

(57) ABSTRACT

An injection device for injecting a composition contained in a medical container comprising: a body configured to receive the medical container in a fixed position relative to the body, spring-loaded piston rod translationally movable inside the body along a spring axis, between a proximal rest position and a distal operative position wherein the spring-loaded piston rod engages a stopper of the medical container, and a selective blocking mechanism comprising a braking member selectively tiltable relative to the piston rod between a blocking position wherein the braking member impinges on the piston rod so as to prevent any translational movement of the spring-loaded piston rod in a distal direction by a bracing effect and a releasing position wherein the braking member disengages from the piston rod so as to allow the piston rod to move towards the distal operative position under the spring force.

18 Claims, 11 Drawing Sheets

(52) U.S. Cl.
CPC ............... *A61M 2005/2073* (2013.01); *A61M 2005/2407* (2013.01)

(58) Field of Classification Search
CPC .... A61M 2005/2407; A61M 2205/276; A61M 5/24; A61M 5/31566; A61M 5/31565; A61M 5/31576; A61M 5/31578; A61M 5/31581

See application file for complete search history.

INJECTION DEVICE FOR INJECTING A COMPOSITION CONTAINED IN A MEDICAL CONTAINER

CROSS-REFERENCE TO RELATED APPLICATIONS

This application is the United States national phase of International Application No. PCT/EP2019/052393 filed Jan. 31, 2019 and claims priority to European Patent Application No. 18305109.3 filed Feb. 2, 2018, the disclosures of which are hereby incorporated by reference in their entirety.

TECHNICAL FIELD OF THE INVENTION

The invention relates to an assisted injection device for injecting a composition contained in a medical container. The injection device allows the user to control the injection by selectively allowing or stopping the injection, and makes the injection easier for a user who needs to provide less effort for injecting the composition, especially a composition with a high viscosity.

TECHNICAL BACKGROUND

Prefilled injection devices are common containers to deliver drugs or vaccines to patients and include syringes, cartridges and autoinjectors or the like. They usually comprise a sealing stopper in gliding engagement into a container, the container being filled with a pharmaceutical composition in order to provide the practitioners with a ready-to-use injection device for patients.

A container has a substantially cylindrical shape, and comprises a proximal end able to be stoppered by a sealing stopper, a distal end wherein the pharmaceutical composition is expelled from the container, and a lateral wall extending between the proximal end and the distal end of the container. In practice, the sealing stopper is aimed at moving, upon the pressure exerted by a piston rod, from a proximal end of the container towards the distal end of the container, thereby expelling the drug contained into the container.

When compared to empty injection devices that are filled with a vial-stored pharmaceutical composition just prior to the injection to the patient's body, the use of prefilled injection devices leads to several advantages. In particular, by limiting the preparation prior to the injection, the prefilled injection devices provide a reduction of medical dosing errors, a minimized risk of microbial contamination and an enhanced convenience of use for the practitioners. Furthermore, such prefilled containers may encourage and simplify self-administration by the patients which allows reducing the cost of therapy and increasing the patient adherence. Finally, prefilled injection devices reduce loss of valuable pharmaceutical composition that usually occurs when a pharmaceutical composition is transferred from a vial to a non-prefilled injection device. This results in a greater number of possible injections for a given manufacturing batch of pharmaceutical composition thus reducing buying and supply chain costs.

In certain cases, the injection of the pharmaceutical composition contained in the container with a manual injection device, such as a syringe, can be difficult to carry out, due to the force that needs to be applied onto the piston rod for expelling it. This occurs for example when the pharmaceutical composition has a high viscosity, and/or when the injection is carried out manually by a user that cannot push on the piston rod strongly enough with his fingers, for example when suffering from rheumatoid arthritis or from any type of disease affecting the user's hand or fingers. The injection may be a self-injection or may be performed by a user, such as a health care professional, to another person. In the case of healthcare professionals performing repetitive injections of viscous drugs to patients, the repetition of the same gesture requiring high force applied on the plunger rod to make the injection may cause repetitive strain injuries.

Autoinjectors can assist the user in performing an automatic injection of the pharmaceutical composition. They usually comprise an injection button the user needs to press in order to start the injection.

The injection carried out with an autoinjector is automatic, which means that once the user has pressed the injection button to move the piston, the injection starts and keeps going until the entirety of the pharmaceutical composition is injected.

A consequence is that once the user has triggered the injection by pushing the button, the injection cannot be stopped and restarted again. In particular, carrying out multiple injection sequences of fractions of the pharmaceutical composition while stopping the injection between two consecutive sequences is also not possible.

This lack of control of the injection can generate pain and anxiety to the user, and may lead the user to be unable to perform the injection correctly.

Moreover, similarly to manual injection devices, autoinjectors can encounter difficulties for injecting a pharmaceutical composition with a high viscosity, mainly due to an insufficient force applied to the piston by the injection mechanism. Hence, the pharmaceutical composition is not expelled from the container, or at most expelled at a very low speed.

BRIEF DESCRIPTION OF THE INVENTION

In view of the foregoing, an object of the invention is to provide an assisted injection device for injecting a pharmaceutical composition contained in a medical container that overcomes the drawbacks of the known devices.

The invention aims to provide an injection device which allows the user to control the injection, in particular to stop the injection then starting it again and to adjust the injection rate while performing the injection.

The invention aims also to provide such a device that allows for an easier injection of the pharmaceutical composition compared to the existing injection devices, in particular when the pharmaceutical composition has a high viscosity and/or when the user has a reduced physical strength.

One object of the invention is an injection device for injecting a composition contained in a medical container, comprising:

a body configured to receive the medical container in a fixed position relative to the body, a spring-loaded piston rod translationally movable inside the body along a spring axis, between a proximal rest position and a distal operative position wherein the spring-loaded piston rod engages a stopper of the medical container, and a selective blocking mechanism comprising a braking member selectively tiltable relative to the piston rod between a blocking position wherein the braking member impinges on the piston rod so as to prevent any translational movement of the spring-loaded piston rod in a distal direction by a bracing effect and a releasing position wherein the braking member disengages from the piston rod so as to allow the piston rod to move towards the distal operative position under the spring force.

The blocking of the piston rod by the braking member being in a given tilted position relies on a bracing effect.

By "bracing effect" is meant in the present text a blocking of a first part in sliding engagement with a second part along an axis due to friction, even if a force is applied to the first part in the axial direction. In the present case, the first part is the piston rod and the second part is the braking member, which, when tilted in the blocking position, exerts a friction force onto the piston rod sufficient to generate said bracing effect.

The bracing effect results from a torque that urges the braking member in rotation relative to an axis that is preferably perpendicular to the spring axis. This causes the braking member to abut the plunger rod in at least two diametrically opposite points of the plunger rod.

In this application, the "distal direction" is to be understood as meaning the direction of injection, with respect to the medical container the device of the invention is to be mounted on. The distal direction corresponds to the travel direction of the piston rod during the injection, the pharmaceutical composition contained initially in the medical container being expelled from said medical container. The "proximal direction" is to be understood as meaning the opposite direction to said direction of injection.

In this application, the term "orthogonal" designates two axes—extending in a three-dimensional space—that are parallel to respective axes that intersect at a right angle. Said orthogonal axes may belong to a same plane and thus intersect (in this case they are perpendicular), or not.

In this application, a "selective blocking mechanism" refers to a mechanism that may be moved from the blocking position to the actuating position or conversely by the user, during the use of the injection device, to either proceed to the injection or stop the injection. Hence, by selectively actuating or blocking the selective blocking mechanism, the user can start or stop the injection of the composition contained in the medical container at any time of the injection.

According to other optional features of the device of the invention:

The selective blocking mechanism further comprises:
a lever pivotably mounted on the body about a pivot axis orthogonal to the spring axis, comprising an actuation zone at a first distance from the pivot axis, and
a connecting rod including a first end coupled to the lever by a pivot axis opposite the actuating zone relative to the pivot axis, at a second distance from the pivot axis, and a second end coupled to the braking member,
the lever being pivotable between a rest position wherein the connecting rod constrains the braking member in the blocking position, and an actuating position wherein the connecting rod releases the braking member to the releasing position.

The selective blocking mechanism thereby provides a lever effect, which facilitates the injection of high viscosity compositions and/or reduce the force required for the user to carry out the injection. The user may inject the composition or stop the injection at any time by either pushing the lever or releasing the lever respectively.

The lever is coupled to the spring loaded piston rod such that the spring force urges the lever to the rest position. Hence, the spring force of the spring loaded piston rod is used for both moving and blocking the piston rod so as to respectively start and stop the injection.

The first distance is advantageously greater than the second distance, preferably at least twice greater than the first distance.

The selective blocking mechanism further comprises a spring member configured to exert a spring force on the braking member so as to constrain the braking member in the blocking position. Hence, the spring force of the spring loaded piston rod is used only to move the piston rod.

The spring member is connected to the body and to the connecting rod.

The spring member is connected to the body and to the braking member.

The braking member comprises an actuation zone configured for moving the braking member from the blocking position to the releasing position, the selective blocking mechanism further comprising a spring member that urges the braking member to the blocking position.

The spring member is arranged around the piston rod directly in contact with the braking member.

The braking member is preferably a plate provided with a through hole and the spring-loaded piston rod extends through said hole, the inner surface of the hole being configured to impinge on the piston rod when the plate is in the blocking position.

The through hole has a dimension greater than the piston rod, said dimension being configured such that when the braking member is tilted in the blocking position, at least a part of the circumference of the through hole contacts an outer wall of the piston rod.

In the releasing position, the plate is orthogonal to the spring axis.

The body comprises a container holder system configured to receive at least a portion of the medical container and to hold the medical container aligned with the movement direction of the spring-loaded piston rod so that when moving from the proximal rest position to the distal operative position, the spring-loaded piston rod engages the stopper of the medical container and pushes the stopper in the medical container to inject the composition.

The container holder system comprises:
an opening provided in the distal wall of the body that leads to a housing adapted to receive at least a portion of the medical container in a position aligned with the movement direction of the spring-loaded piston rod,
a slot provided in the outer wall of the body that leads to the housing, and
an insert adapted to be inserted in the slot to contact the medical container and to maintain the medical container in a fixed position in the housing.

The container holder system comprises:
a slot provided in the outer wall of the body that leads to a housing, configured to receive at least a portion of the medical container and to maintain the medical container in a fixed position aligned with the movement direction of the spring-loaded piston rod, and
a through groove provided in the distal wall of the body, continuous with the slot and extending in the distal wall from the slot, the groove being configured to guide the medical container inserted via the slot to the housing.

The injection device is advantageously configured to be handheld.

BRIEF DESCRIPTION OF THE DRAWINGS

Further features and advantages of the invention will become apparent from the detailed description to follow, with reference to the appended drawings.

DETAILED DESCRIPTION OF EMBODIMENTS OF THE INVENTION

Figure 1:
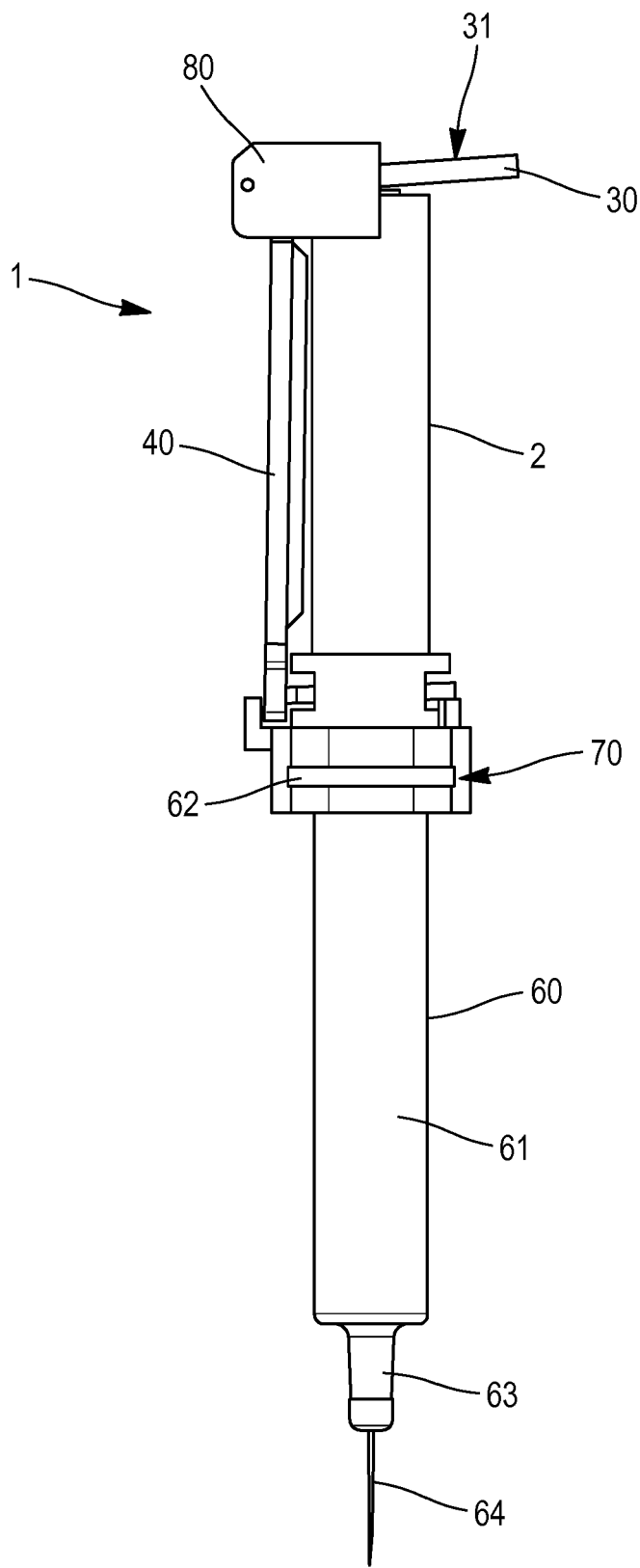
FIG. 1 is a side view of a first embodiment of the injection device of the invention.

The invention proposes an injection device for injecting a composition contained in a medical container.

Prior to the injection, the medical container is filled with the composition intended to be injected, and stoppered with a stopper inserted therein. The stoppered medical container is then mounted on the device, and the injection of the composition can be carried out.

A first embodiment of the injection device is represented in FIGS. 1, 2, and 3A-B. According to this embodiment, the injection device 1 comprises a body 2 adapted to be held by a user's hand. To this end, the body 2 has preferably a cylindrical shape so as to make its handling easier, and is preferably made of a grip material that makes the user's hand adhere to the body. That way, the user can firmly handle the device throughout the injection of the composition.

The body 2 of the device further comprises a container holder system 70 configured to receive and to maintain the medical container 60 in a fixed position while performing the injection.

The medical container 60 comprises a body 61 including a proximal end 62 preferably provided with a flange, and a distal end having a tip 63 and a needle 64 extending from thereon. The needle 64 may be covered by a cap (not represented) to prevent any injury when handled before use.

Figures 2, 2A:
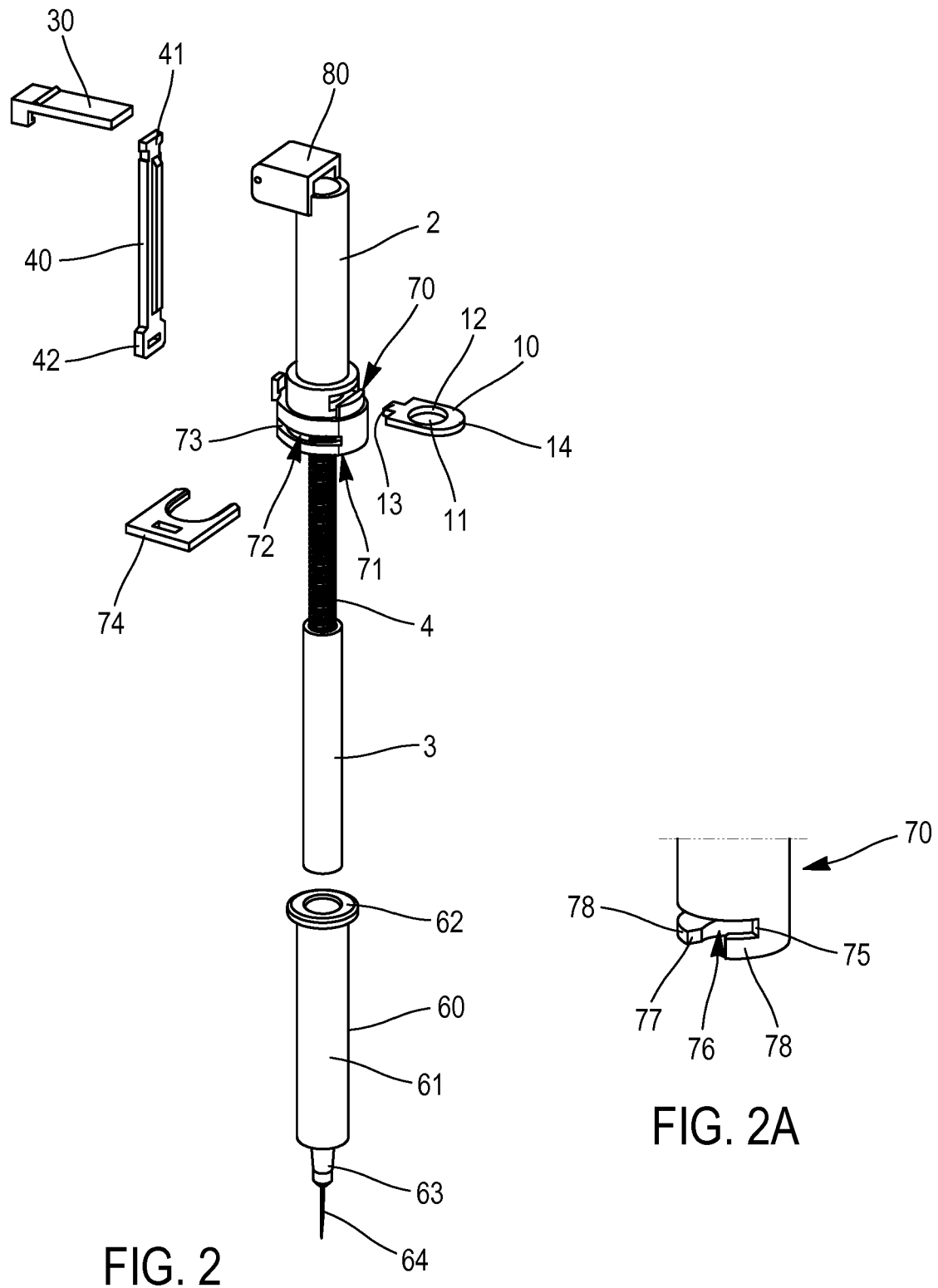
FIG. 2 is an exploded perspective view of the components of the injection device illustrate in FIG. 1.
FIG. 2A is a perspective view of an embodiment of the container holder system.

According to a first embodiment illustrated on FIGS. 1 and 2, the container holder system 70 includes an opening 71 provided at the distal end of the body 2 that leads to a housing 72 adapted to receive the proximal end 62 of the medical container 60. The container holder system further includes a slot 73 provided in the outer wall of the body 2 in communication with the housing, and an insert 74 adapted to be inserted into the slot 73 until coming into contact with the proximal end 62 of the medical container for securing it in the housing 72. The insert 74 is advantageously in the form of a fork with two branches so as to grip the body 61 of the container inserted in-between. The proximal end of the container then abuts the insert thereby avoiding the container to fall off the device.

In a practical way, the proximal end of the container 60 is inserted through the opening 71 and moved in a proximal direction until being positioned in the housing 72 and the insert 74 is then inserted radially in the slot 73 to secure the medical container 60 in a fixed position relative to the body 2.

This embodiment is particularly useful when the container is a syringe or the like as the proximal end of the container is a flange adapted to abut the insert.

Alternatively, when the container is a cylinder or the like (with no proximal flange), the configuration of the container holder system of the first embodiment may be adapted accordingly. According to a preferred embodiment (not represented), the housing extends distally in a portion of the body of the device, and is configured to receive the entire body of medical container. Advantageously, in this situation, only the tip and a needle of the medical container project distally out of the body of the device. Of course, this preferred embodiment may also be appropriate when the medical container is a syringe or the like, the housing being adapted accordingly to accommodate the flange of the medical container.

In a practical way, the container is inserted in the housing through a lateral opening (not represented) provided in the peripheral surface of the body. To that end, the dimensions of the lateral opening correspond substantially to the dimensions of the body of the medical container. The insert is then inserted in the slot until being in contact with a shoulder extending between the distal end of the body and the tip of the medical container. Hence, the shoulder abuts the insert, which thereby maintains the container in a fixed position in the housing.

According to a second embodiment illustrated on FIG. 2A, the container holder system 70 includes a slot 75 provided in the outer wall of the body 2 that leads to a housing 76 adapted to receive the proximal end 62 of the medical container 60.

The container holder system 70 further includes a through groove 77 provided in the distal wall of the body, continuous with the slot 75 and extending in the distal wall from the slot 75. In a practical way, the proximal end of the container is inserted through the slot 75 and moved in a radial direction along the groove 77 until being positioned in the housing 76 where the medical container 60 is maintained in a fixed position relative to the body 2. The groove 77 separates two projecting parts 78 against which the proximal end of the medical container can abut, thereby preventing the container from falling off the groove.

To this end, the inner surface of the groove 77 contacts the body 61 of the container 60. In particular, the groove 77 can be configured to prevent the container 60 inserted herein from moving radially, unless the container is moved by a user. The groove is preferably made of a rigid and smooth material, such as rigid plastic or metal (e.g. aluminum, stainless steel) for example, for making the insertion of the container therein easier, as well as contributing to maintain the container in a fixed position in the housing 76 during the injection.

This embodiment is particularly useful when the container is a syringe or the like as the proximal end of the container is a flange adapted to abut the projecting parts.

Alternatively, when the container is a cylinder or the like (with no proximal flange), the configuration of the container holder system of the second embodiment may be adapted accordingly.

The injection device 1 further comprises a spring-loaded piston rod 3 that extends inside the body 2 along a longitudinal axis (A), called spring axis. The spring 4 of the piston rod is arranged inside the body 2, coaxially and in contact with the piston rod 3. The medical container 60 maintained in the container holder system 70 is aligned with the axis (A). In that way, the spring-loaded piston rod 3 is translationally movable inside the body 2 of the device under the force of the spring 4 along the axis (A), between a proximal rest position and a distal operating position wherein the piston rod 3 engages the stopper 65 of the medical container 60 and pushes said stopper into the medical container.

The injection device 1 also comprises a selective blocking mechanism for selectively blocking or releasing the piston rod 3 based on a bracing effect.

According to the first embodiment of the device, the selective blocking mechanism comprises a lever 30 pivotably mounted on the body 2, preferably on a proximal side of the body 2, about a pivot axis (B) orthogonal to the spring axis (A). The lever 30 is preferably mounted on an intermediate piece 80 of the body 2 of the device, which includes mechanical means for mounting the lever 30 thereon. The intermediate piece 80 may be adapted to be mounted on the body 2, or may be made from a single piece with the body.

An actuation zone 31 is provided on the lever 30, at a first (non-zero) distance from the pivot axis (B). The actuation zone 31 is integral with the lever 30 and constitutes a button intended to be pushed by the user in a distal direction, in order to move the lever 30 in a tilting motion about the pivot axis (B), from a first position called rest position to a second position called actuating position.

The selective blocking system further comprises a connecting rod 40 including a first end 41 pivotably coupled to the lever 30 according to a pivot axis (C) opposite the actuating zone 31 relative to the pivot axis (B), at a second distance from the pivot axis (B). The pivot axis (C) is orthogonal to the spring axis (A). The coupling of the lever 30 and the connecting rod 40 is preferably achieved by a stud (not represented) provided on one of the lever 30 or the connecting rod 40 and corresponding holes (not represented) provided on the other one adapted to receive the stud.

The selective blocking mechanism further comprises a braking member 10.

According to a preferred embodiment, and as illustrated in FIGS. 1 and 2, the braking member 10 is a plate that extends radially, that is, in a direction substantially orthogonal to the spring axis (A). The plate 10 is provided with a hole 11 configured to receive the piston rod 3. This way, the piston rod 3 crosses the plate via the hole 11, and an inner surface 12 of the hole faces the piston rod 3.

The plate defines a first portion 13 pivotably coupled to the second end 42 of the connecting rod 40, and a second portion 14, opposite the first portion 13 relative to the spring axis (A) of the piston rod 3, configured to be supported by a supporting surface 6 of the body 2 of the device.

The plate 10 is selectively tiltable relative to the piston rod 3, by selectively moving the connecting rod 40, between a blocking position and a releasing position. In the blocking position, the plate 10 is tilted relative to the piston rod 3, and impinges on the piston rod 3 via a contact surface between the inner surface 12 of the hole 11 at the first and second portions 13, 14 of the plate and the piston rod 3. At the same time, the second portion 14 bears onto the supporting surface 6. Hence, the plate 10 prevents the piston rod 3 from moving translationally in the distal direction along the axis (A) thanks to the bracing effect. In the releasing position, the plate 10 disengages from the piston rod 3, so that there is no more contact between the plate 10 and the piston rod 3. Hence, the piston rod 3 is allowed to move towards the distal operative position under the spring force.

By selectively pushing or releasing the actuation zone 31 of the lever 30, the user can start or stop the injection of the pharmaceutical composition contained in the medical container.

Figure 3A:
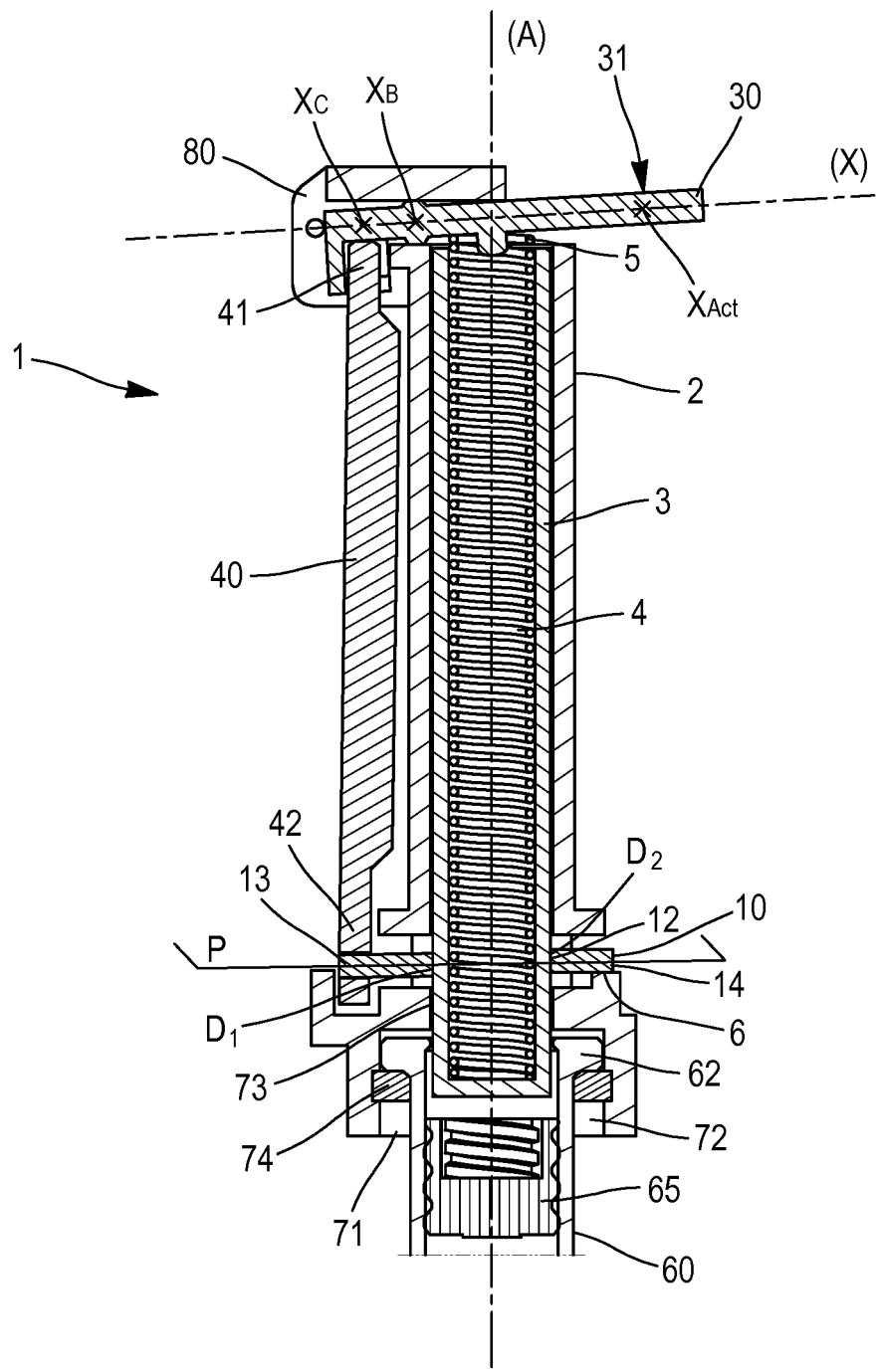
FIGS. 3A and 3B are side sectional views from a first side of the device illustrated in FIG. 1, wherein the selective blocking mechanism respectively blocks and allows the movement of the piston rod.

As illustrated in FIG. 3A, when the actuation zone 31 is released, the lever 30 is in the rest position. The spring 4 is in a compressed state and tends to move to a released state, thereby pressing onto the lever 30 via its proximal end 5. The pressure applied by the spring 4 onto the lever 30, constrains said lever in the rest position. The lever 30 presses onto the connecting rod 40 via their connection according to the axis (C), and the connecting rod 40 presses onto the first portion 13 of the plate 10. The first portion 13 of the plate 10 offsets longitudinally relative to the second portion 14, making the plate 10 itself offset relative to the piston rod 3. This situation is illustrated in FIG. 3A with a plane P, containing the plate 10, close to but not orthogonal to the spring axis (A).

In this situation, a torque defined by two forces of opposite direction, that may be represented by two opposite forces parallel to the spring axis (A) and applied onto the first portion 13 and the second portion 14 respectively of the plate 10, urges the plate 10 in rotation relative to an axis that is perpendicular to the plane of the sheet of FIG. 3A and to the spring axis (A). This causes the plate 10 to abut the plunger rod at two diametrically opposite points of the plunger rod, the contacting points $D_1$ and $D_2$, by a bracing effect.

The plate 10 is thus constrained in the blocking position by the connecting rod 40, wherein the inner surface 12 of the plate contacts and blocks the piston rod 3 by friction via the contacting points $D_1$ and $D_2$.

Figure 3B:
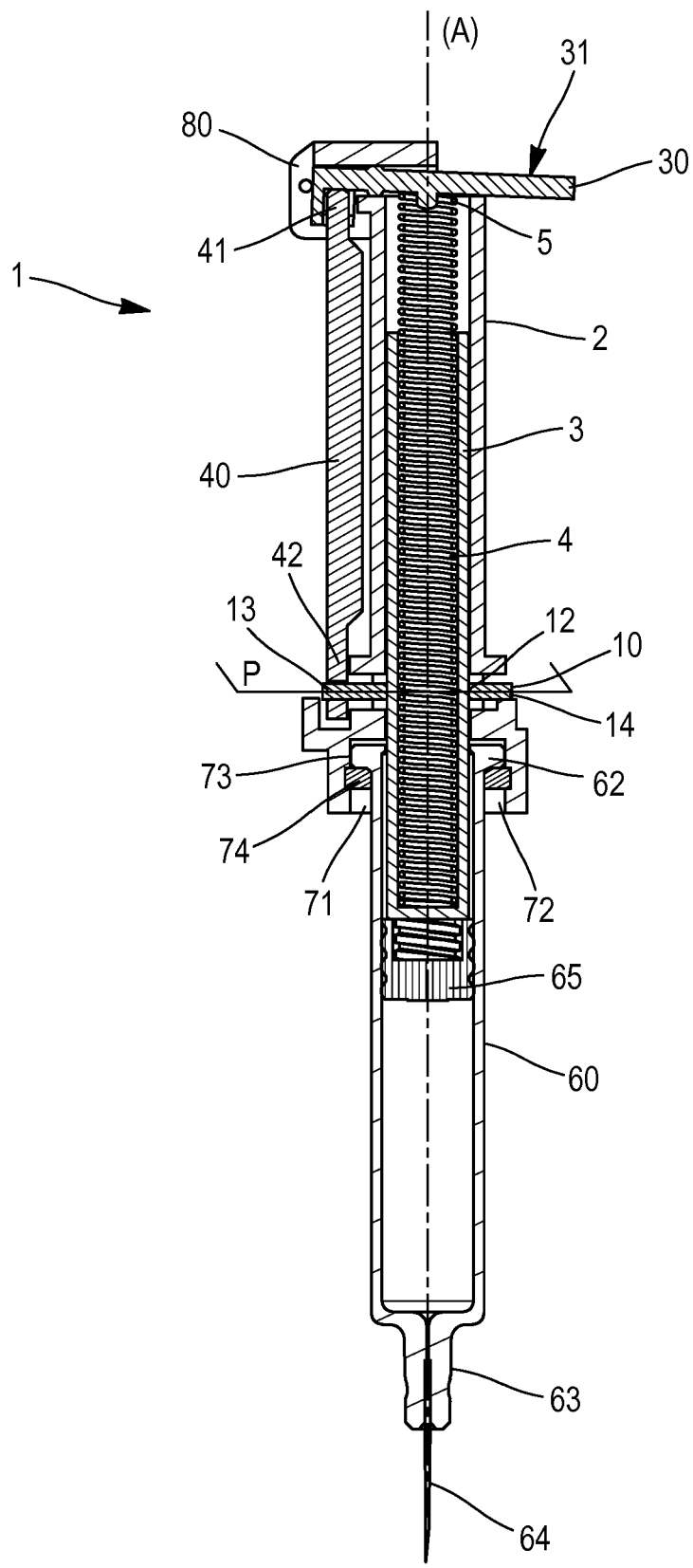

As illustrated in FIG. 3B, when the user pushes the actuation zone 31 in a distal direction, the lever 30 moves in a tilting motion about the pivot axis (B) and pulls the connecting rod 40 via their connection according to the axis (C) in a proximal direction. By moving to the proximal direction, the connecting rod 40 pulls the first portion 13 of the plate 10 in the proximal direction. The second portion 14 is pressed in a distal direction against the supporting surface 6 of the body 2. This causes the plate 10 to move in a tilting motion relative to the piston rod 3, thereby cancelling the offset between the first and second portion 13, 14 of the plate 10. This situation is illustrated in FIG. 3B wherein the plane P containing the plate 10 is orthogonal to the spring axis (A).

The plate 10 thus disengages from the piston rod 3, moving from the blocking position to the releasing position. As there is no more contact between the plate 10 and the piston rod 3, said piston rod is allowed to move translationally with the spring force of the spring 4 in a distal direction, to a distal operative position wherein the piston rod 3 engages the stopper 64 and pushes said stopper in the medical container 60. The composition is thus expelled from the medical container. In this position, the spring 4 is at least partially released.

The braking member moves in a tilting motion about a tilting point that may be aligned with the spring axis (A), or remote from the spring axis (A), thereby describing a corresponding tilting angle. In the situation of the first embodiment, as well as the following second embodiment, the plate 10 is partially supported by the supporting surface 6, such that the tilting point is located in the vicinity of the contact surface between the second portion 14 of the braking plate 10 and the supporting surface 6.

The tilting angle mainly depends on the shape of the braking member, in particular the shape of the surface of the braking member configured to contact the piston rod, and the configuration of the braking member in the device.

As long as the user keeps pushing the actuation zone 31, the plate 40 remains in the releasing position, disengaged from the piston rod 3, the piston rod 3 keeps moving with the release of the spring 4, and the injection continues.

During injection, when the user releases the actuation zone 31, the lever 30 moves back in a tilting motion to its rest position thanks to the spring force of the spring 4, the plate 10 moves back in the blocking position thereby reimpinges on the piston rod 3, and the device 1 returns in the situation described previously, the piston rod 3 being in a more distal position than previously.

As such, the user can start or stop the injection simply by pressing the actuation zone 31 during a certain amount of time or by releasing it.

As described previously, when the user pushes the actuation zone 31, the lever 30 moves from the rest position to the actuating position, and the piston rod 3 is moved by the spring force of the spring 4. Therefore, the spring force is used for both moving and blocking the piston rod 3 so as to respectively start and stop the injection.

The bracing effect mainly depends on:
- the force applied onto the braking member for maintaining it in the blocking position. This force is applied in a direction parallel to the spring axis (A), towards the braking member, and the intensity of said force needs to be sufficient in order to achieve an effective blocking of the piston rod. According to the first embodiment, this force is applied by the connecting rod 40 onto the first portion 13 of the plate 10, and corresponds to the elastic force of the spring 4 that is transmitted to the connecting rod 40 by the lever 30;
- the position of the tilting point of the braking member relative to the spring axis (A). In order to achieve an effective blocking of the piston rod, the tilting point is positioned so that the force applied onto the braking member is as explained above. In particular, the greater the distance between the tilting point and the axis (A), the greater the force applied onto the braking member;
- the friction between the braking member and the piston rod. Such friction depends on structural features of the braking member and the piston rod, in particular their shape (that may be adjusted to maximize their contact surface) and their mechanical properties such as their constitutive material (that may be selected depending on their coefficient of friction) for example; and
- the tilting angle of the braking member relative to the spring axis (A). Such tilting angle depends on the structural features of the braking member. According to the first embodiment, the tilting angle depends on the difference between the diameter of the hole 11 of the plate 10 and the diameter of the piston rod 3.

Moreover, the selective blocking mechanism provides a lever effect. To illustrate this, the position $X_{Act}$ of the actuation zone 31, the position $X_B$ of the pivot axis (B), and the position $X_C$ of the pivot axis (C) are represented in FIG. 3A on an axis (X) extending along the lever 30, and sensibly orthogonal to the spring axis (A). $X_{Act}$ and $X_C$ are projections in a direction parallel to the axis (A) of the central point of the actuation zone 31 and the axis C respectively on the axis (X). $X_B$ is the intersecting point of the axis (B) with the axis (X).

The distance $D_{XAct-XB}$ between $X_{Act}$ and $X_B$ is greater than the distance $D_{XC-XB}$ between $X_C$ and $X_B$, along the axis (X). This induces a lever effect that allows the user to push the actuation zone 31 with a reduced force compared to the braking force.

The lever ratio LR is defined as follows:

$$LR = \frac{1}{\left|\frac{D_{XAct-XB}}{D_{Xc-XB}}\right|}$$

It follows from this formula that the greater the distance $D_{XAct-XB}$ relative to the distance $D_{XC-XB}$, the lower the lever ratio, and the greater the lever effect.

The lever effect is also observed for the transmission of the elastic force of the spring 4 to the connecting rod 40 via the lever 30. Indeed, in reference to FIG. 3A, the spring 4 is connected to the lever 30 between $X_{Act}$ and $X_B$, whereas the connecting rod 40 is connected to the lever 30 between $X_B$ and $X_C$. Therefore, the force applied by the connecting rod 40 onto the plate 10 is greater than the force applied by the spring 4 onto the lever 30. Hence, the braking force is greater than the spring force.

This lever effect is particularly advantageous, since a spring with a high elastic force may be used to facilitate the injection of high viscosity compositions, while still ensuring the blocking of the piston rod and requiring a limited force to use the device.

The bracing effect and the lever effect presented above in reference to the first embodiment of the device also apply to the second embodiment presented below, notwithstanding the structural and functional differences between said embodiments.

According to a second embodiment, the selective blocking mechanism comprises a spring member 50, configured to exert a spring force on the braking member 10 so as to constrain the braking member in the blocking position. In that manner, the spring 4 of the piston 3 allows for pushing the piston rod 3 from the proximal rest position to the distal operative position to carry out the injection of the composition, whereas the spring member 50 allows for pressing the braking member 10 so as to constrain said braking member 10 in the blocking position. In other terms, contrary to what was previously described in the first embodiment, the spring 4 of the piston 3 is no longer involved in the constraining of the braking member 10 in the blocking position, and the spring force is used only to move the piston rod 3. However, the elastic force of the spring member 50 contributes to the above-described bracing effect.

Different configurations of the spring member 50 in the device are possible, among which a first, a second, a third and a fourth configuration are detailed in the following. In these configurations, the spring 4 of the piston rod 3 is not connected to the lever 30 but to other elements of the device. Hence, the spring 4 does not press the lever 30, but pushes the piston rod 3 when the plate 10 is in the releasing position to carry out the injection.

Figure 4A:
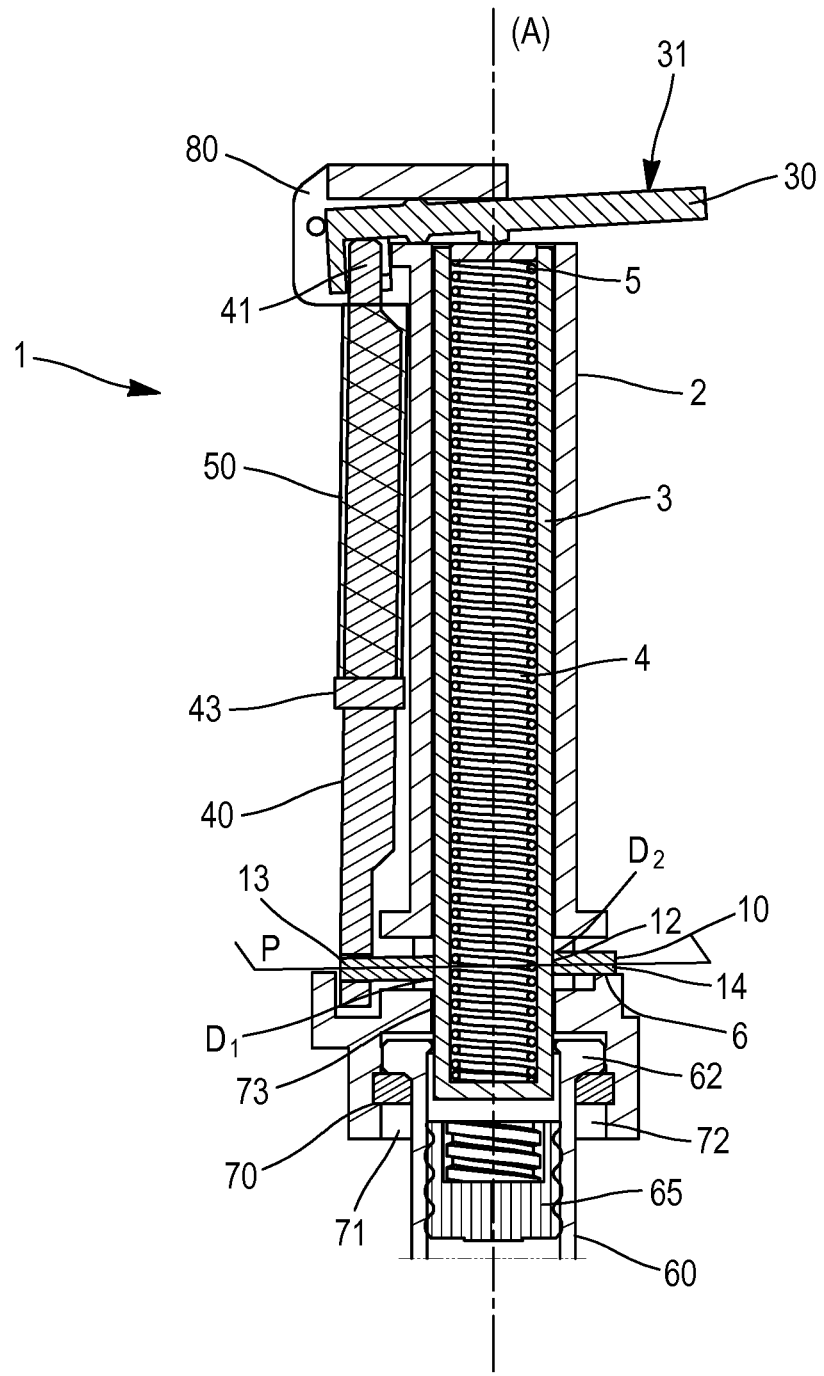
FIG. 4A is a side sectional view of a second embodiment of the injection device of the invention, wherein a spring member is in a first configuration according to an embodiment.
Figure 4B:
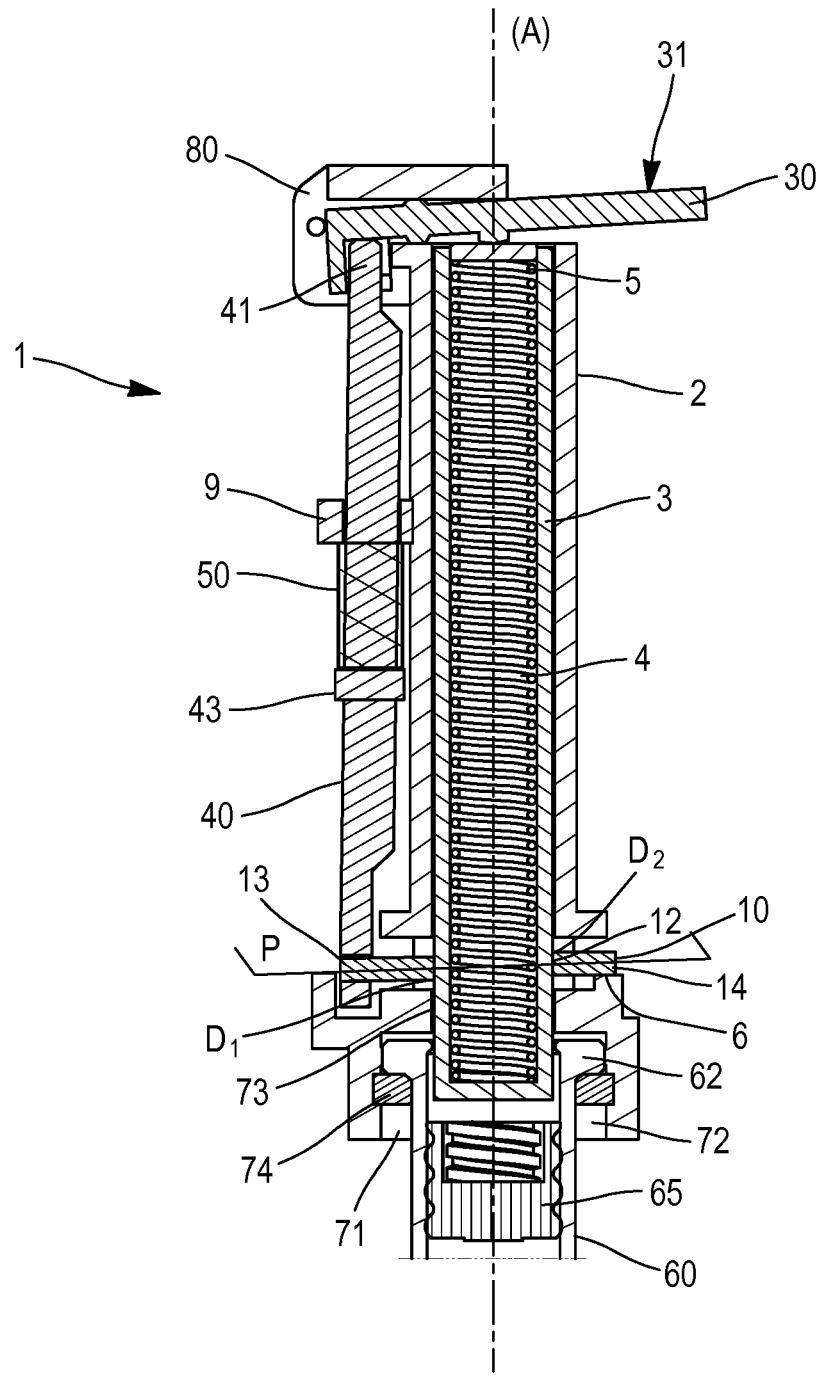
FIG. 4B is a side sectional view of a second embodiment of the injection device of the invention, wherein a spring member is in a first configuration according to another embodiment than FIG. 4A.

According to a first configuration of the second embodiment, one end of the spring member 50 is connected to the body 2 of the device and the other end is connected to the connecting rod 40. According to the embodiment illustrated in FIG. 4A, the spring member 50 is connected to the intermediate piece 80 of the body, and to a flange 43 of the connecting rod 40. According to the embodiment illustrated in FIG. 4B, the spring member 50 is connected to a surface of an intermediate element 9 of the body 2 located between the proximal end and the distal end of the body, and to the flange 43 provided in the connecting rod 40. An advantage of the embodiment of FIG. 4B is that spring members of reduced length can be used. Moreover, the distance between the intermediate element 9 and the proximal and distal ends of the body 2 may be adapted so as to adjust the length of the spring member 50 in the compression state and the resulting spring force.

In this first configuration, the spring member 50 is preferably arranged around the connecting rod 40, so as to simplify the structure and to achieve an optimum stability of the spring member 50.

In this first configuration, the spring member 50 exerts a spring force onto the connecting rod 40, which presses the first portion 13 of the plate in the distal direction, thereby constraining the plate 10 in the blocking position.

Figure 4C:
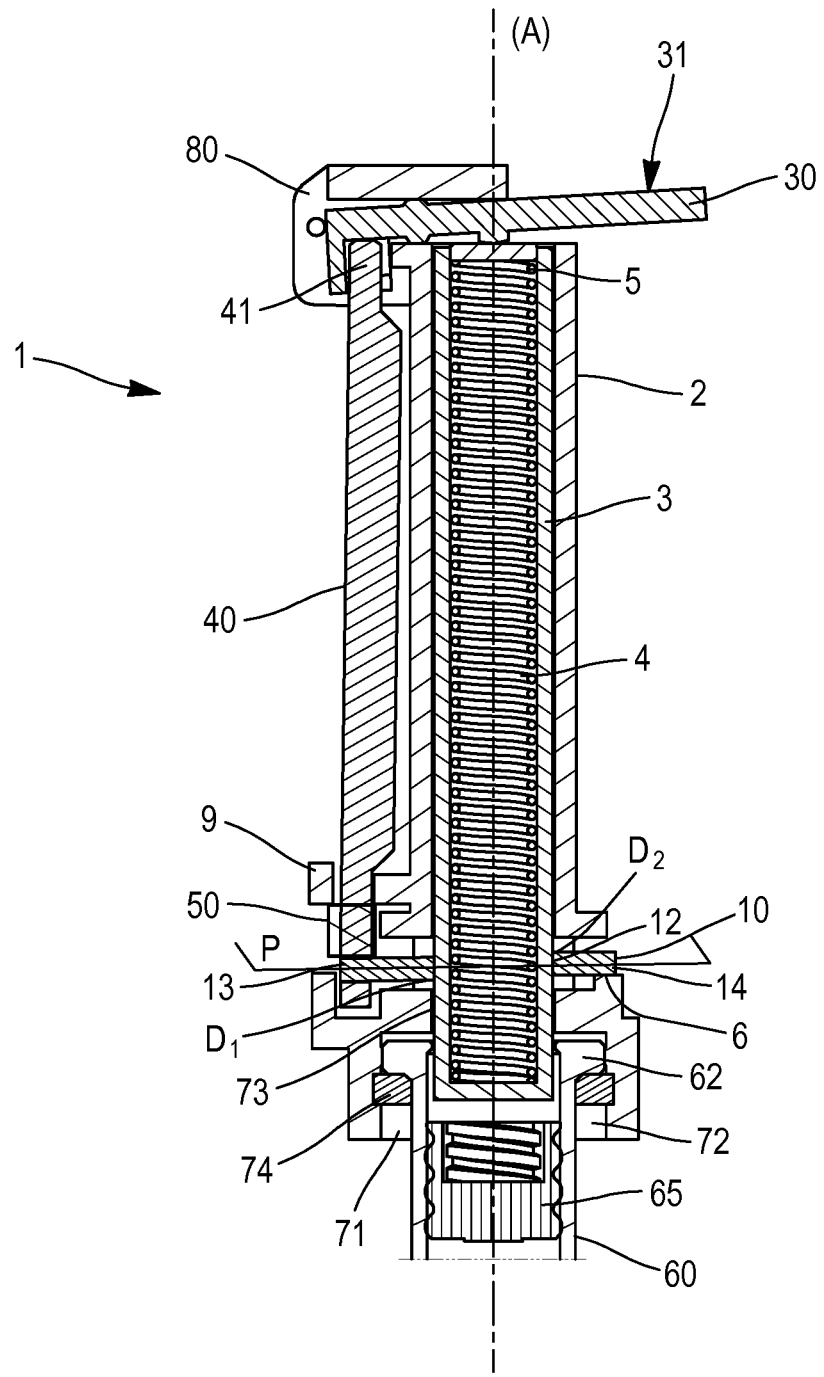
FIG. 4C is a side sectional view of a second embodiment of the injection device of the invention, wherein a spring member is in a second configuration.

According to a second configuration of the second embodiment, one end of the spring member 50 is connected to the body 2 of the device and the other end is connected to the braking member 10. According an embodiment (not represented), the spring member is connected to the intermediate piece 80 of the body, and to the first portion of the plate. According to the embodiment illustrated in FIG. 4C, the spring member 50 is connected to the intermediate element 9 of the body located close to the distal end of the body, and to the first portion 13 of the plate 10. An advantage of the embodiment of FIG. 4C is that spring members of reduced length can be used. Moreover, the distance between the intermediate element 9 and the proximal and distal ends of the body 2 may be adapted so as to adjust the length of the spring member 50 in the compression state and the resulting spring force.

In this second configuration, the spring member 50 may be arranged around the connecting rod 40 or at a distance from the connecting rod, depending on the structural features of the connecting rod 40 and the braking member 10, as well as the desired location of the connecting point of the spring member onto the braking member.

According to a third configuration of the second embodiment (not represented), one end of the spring member is connected to the lever, at a distance from the position $X_B$ of the pivot axis (B) along the axis (X), and the other end is connected to the body of the device, in particular to the proximal end of the body. In this configuration, the spring member exerts a spring force on the lever so as to constrain the lever in the rest position, thereby pressing the first portion of the plate in the distal direction, and constraining the plate in the blocking position. The force applied by the connecting rod onto the plate is greater than the force applied by the spring member onto the lever. Hence, the braking force is greater than the spring force of the spring member. When the user presses the actuation zone of the lever against the spring force of the spring member, the connecting rod pulls the plate in the proximal direction to the releasing position and the spring pushes the piston rod in the distal direction to carry out the injection.

Figure 5:
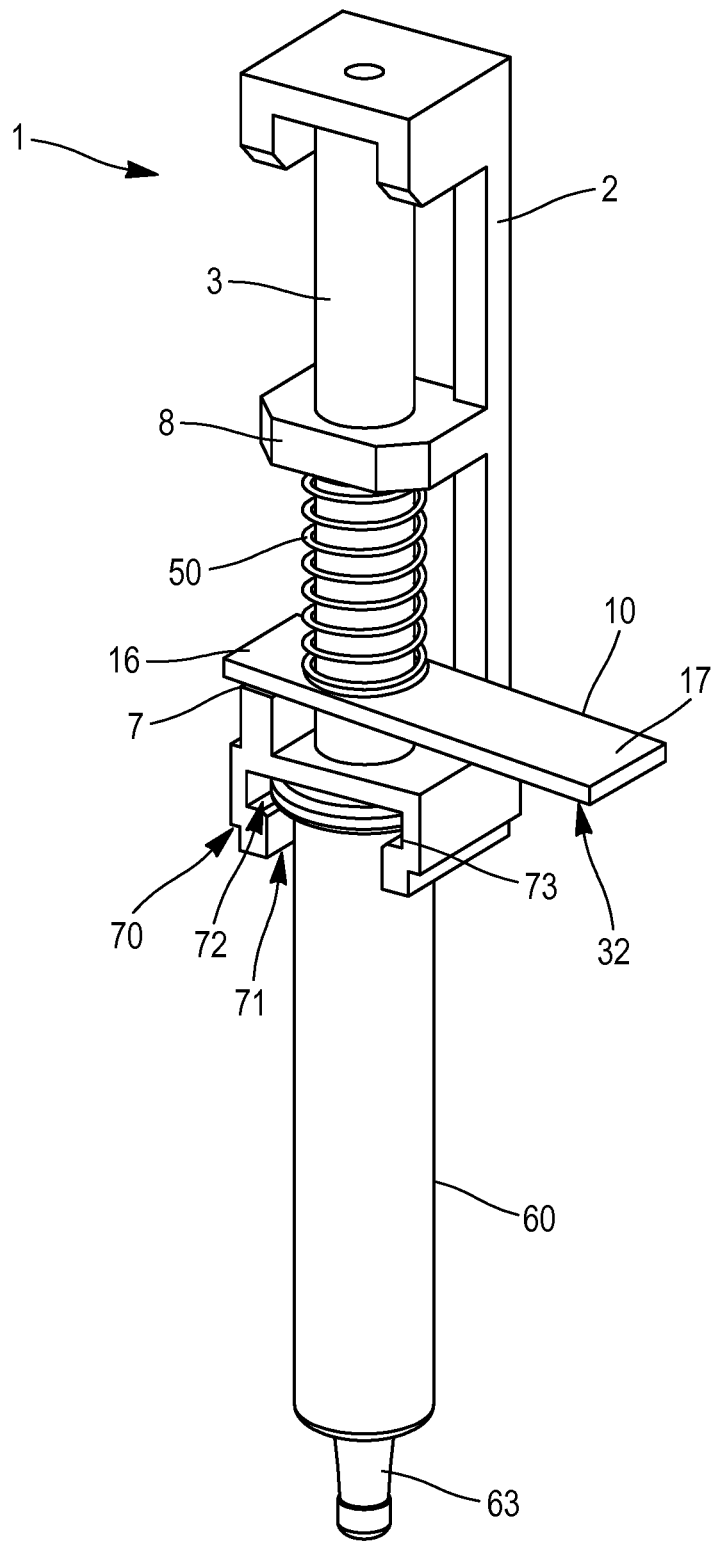
FIG. 5 is a perspective view of the second embodiment of the injection device of the invention, wherein a spring member is in a fourth configuration.
Figure 6:
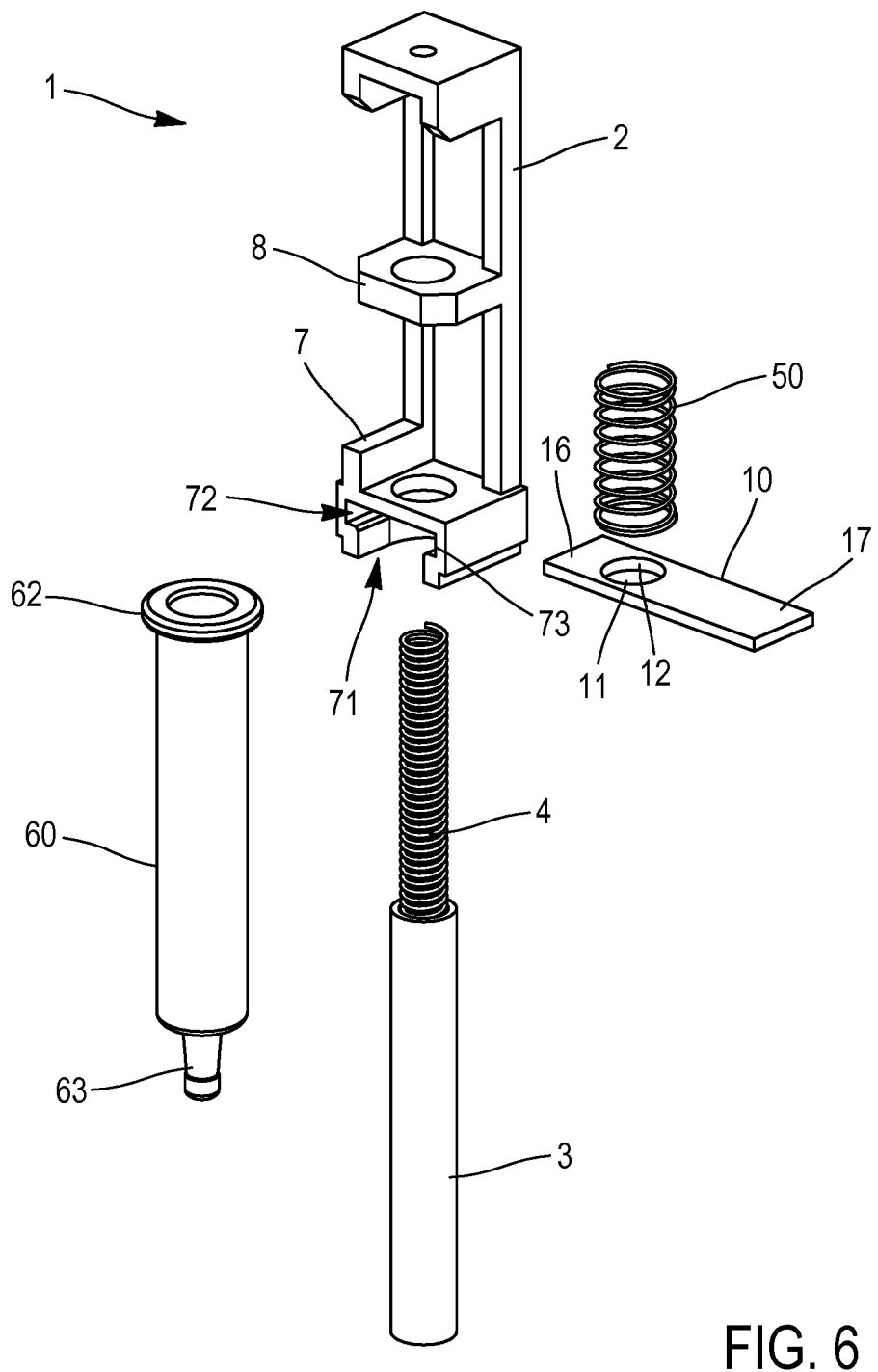
FIG. 6 is an exploded perspective view of the components of the injection device illustrated in FIG. 5.

According to a fourth configuration of the second embodiment, illustrated in FIGS. 5 and 6, the spring member 50 is mounted on the braking member 10, coaxially with the piston rod 3. In this configuration, the braking member 10 is directly actuated by the user that pushes thereon to block or release the piston rod 3.

In more details, the braking member 10 has the general shape of a plate that extends in a substantially radial direction relative to the piston rod. The plate 10 is provided with a hole 11 configured to receive the piston rod 3. This way, the piston rod 3 crosses the plate via the hole 11, and an inner surface 12 of the hole faces the piston rod 3.

The plate 10 defines a first portion 16 which extends radially from the body 2 of the device, and a second portion 17 opposite the first portion 16 relative to the spring axis (A) of the piston rod 3, configured to be supported by a supporting surface 7 of the body 2 of the device.

The spring member 50 includes one end mounted on the body 2 of the device, and another end mounted on the plate 10. Preferably, the spring member 50 is mounted coaxially with the piston rod 3, around said piston rod, the first end of the spring 50 being mounted on the plate 10 so as to surround the hole 11 of the plate. The spring member 50 is in a compressed state, and configured to urge the plate 10 to the blocking position.

As illustrated in FIG. 5, one end of the spring member 50 may be mounted on a surface of an intermediate element 8 of the body 2 located between the proximal end and the distal end of the body. In that manner, springs of reduced length can be used. Moreover, the distance between the element 8 of the body and the first and second ends of the body 2 may be adapted so as to adjust the length of the spring 50 in the compression state and the resulting spring force.

The first portion 16 is provided with an actuation zone 32 at a first (non-zero) distance from the spring axis (A). The actuation zone 32 is integral with the first portion 16 of the plate and constitutes a button intended to be selectively pushed or released by the user in order to selectively move the plate 10 in a tilting motion relative to the spring axis (A), between a blocking position and a releasing position.

In the blocking position, the plate 10 is tilted relative to the piston rod 3, and impinges on the piston rod 3 via a contact surface between the inner surface 12 of the hole 11 at the first and second portions 16, 17 of the plate and the piston rod 3. Hence, the plate 10 prevents the piston rod 3 from moving translationally in the distal direction along the axis (A) by the bracing effect. In the releasing position, the plate 10 disengages from the piston rod 3, so that there is no more contact between the plate 10 and the piston rod 3. Hence, the piston rod 3 is allowed to move towards the distal operative position under the spring force.

The plate 10 illustrated in FIG. 5 is arranged distally from the spring member 50. As such, the user needs to push the actuation zone 32 in the proximal direction in order to move the plate 10 from the blocking position to the releasing position. However, other arrangements of the plate 10 and the spring member 50 are possible, without departing from the scope of the invention.

By selectively pushing or releasing the actuation zone 32, the user can start or stop the injection of the pharmaceutical composition contained in the medical container.

Figure 7A:
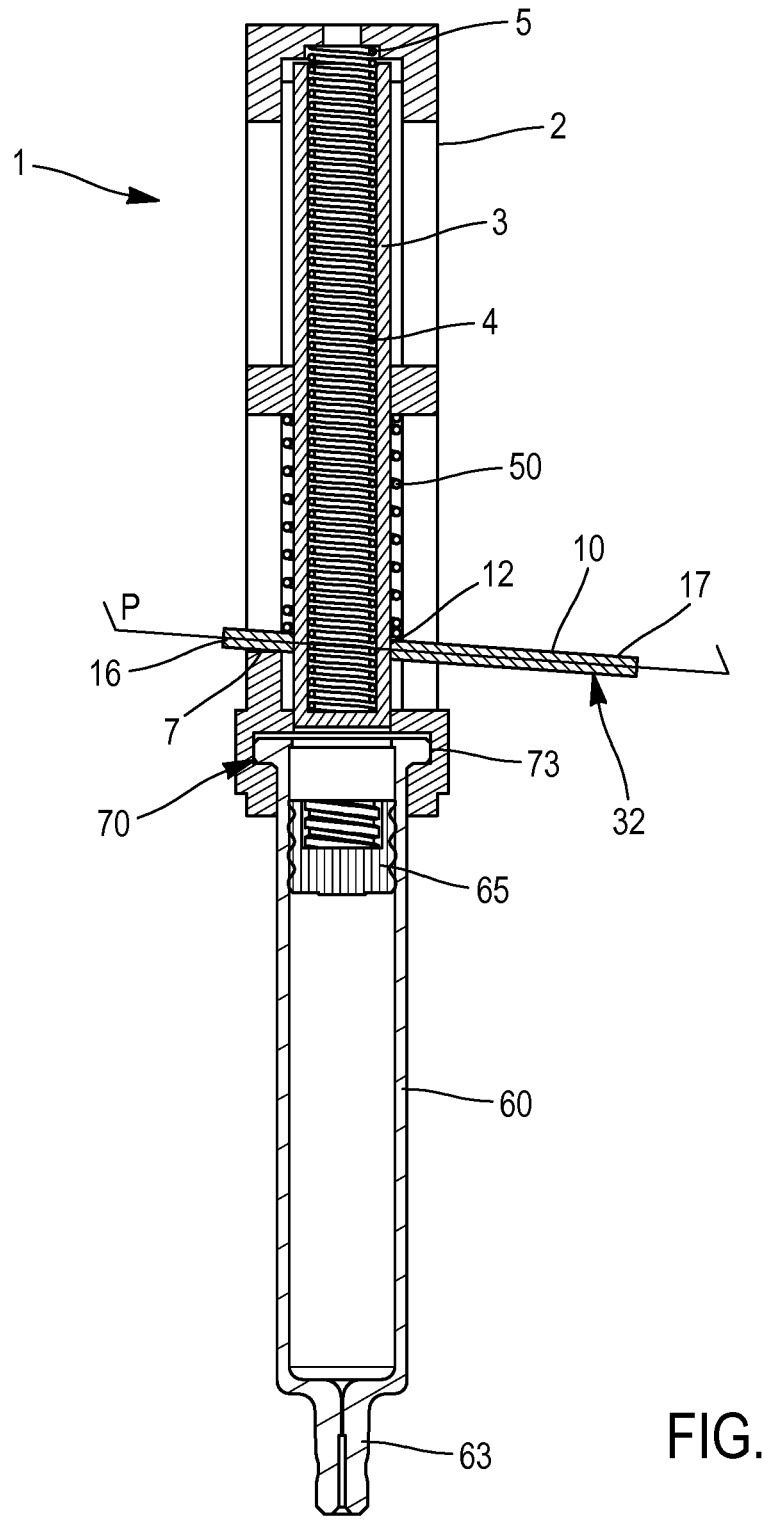
FIGS. 7A and 7B are side sectional views from a first side of the device illustrated in FIG. 5, wherein the selective blocking mechanism respectively blocks and allows the movement of the piston rod.

As illustrated in FIG. 7A, when the actuation zone 32 is released, the plate 10 is constrained in the blocking position by the spring force of the spring 50. The first portion 16 of the plate 10 is longitudinally offset relative to the second portion 17, making the plate 10 itself offset relative to the piston rod 3. This situation is illustrated in FIG. 7A wherein a plane P containing the plate 10 is close to but not orthogonal to the spring axis (A).

Figure 7B:
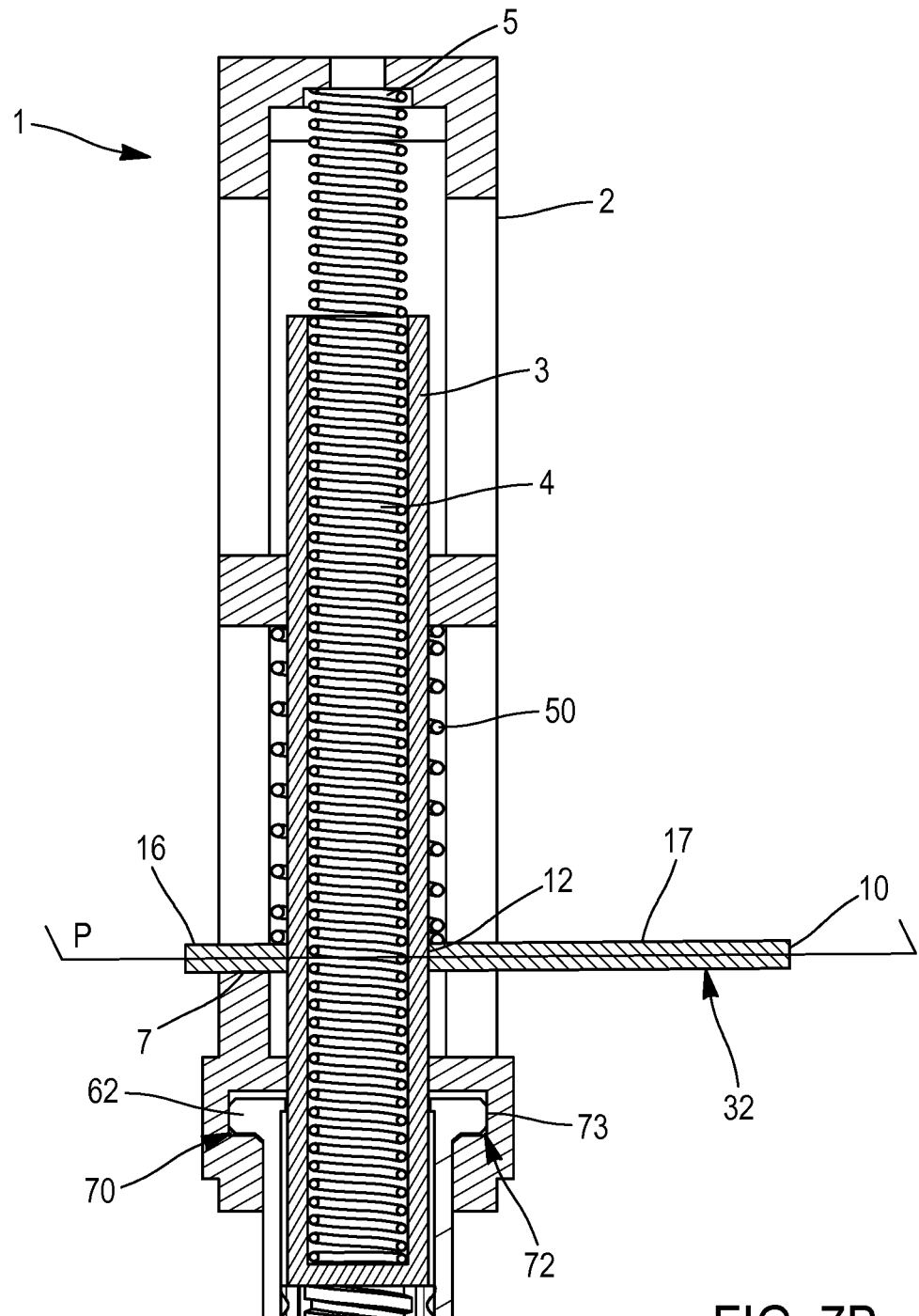

As illustrated in FIG. 7B, when the user pushes the actuation zone 32 in a proximal direction, the first portion 16 of the plate 10 moves in a proximal direction, while the second portion 17 is pressed in a distal direction against the supporting surface 7 of the body 2. This causes the plate 10 to move in a tilting motion relative to the piston rod 3, thereby cancelling the offset between the first and second portion 16, 17 of the plate 10. This situation is illustrated in FIG. 3B wherein the plane P containing the plate 10 is orthogonal to the spring axis (A).

The plate 10 thus disengages from the piston rod 3, moving from the blocking position to the releasing position. As there is no more contact between the plate 10 and the piston rod 3, said piston rod is allowed to move translationally with the spring force of the spring 4 in a distal direction, to a distal operative position wherein the piston rod 3 engages the stopper 64 and pushes said stopper in the medical container 60. The composition is thus expelled from the medical container. In this position, the spring 4 is at least partially released.

As long as the user keeps pushing the actuation zone 32 of the plate 10, said plate 10 remains in the releasing position, disengaged from the piston rod 3, the piston rod 3 keeps moving with the release of the spring 4, and the injection continues.

During injection, when the user releases the actuation zone 32, the plate 10 moves back in a tilting motion to the blocking position thanks to the spring force of the spring 50, thereby re-impinges on the piston rod 3, and the device 1 returns in the situation described previously, the piston rod 3 being in a more distal position than previously.

As such, the user can start or stop the injection simply by pressing the actuation zone 32 during a certain amount of time or by releasing it.

The invention claimed is:

1. An injection device for injecting a composition contained in a medical container comprising:
   a body configured to receive the medical container in a fixed position relative to the body;
   a spring-loaded piston rod translationally movable inside the body along a spring axis, between a proximal rest position and a distal operative position wherein the spring-loaded piston rod engages a stopper of the medical container; and
   a selective blocking mechanism comprising a braking member selectively tiltable at any time during the injection relative to the spring-loaded piston rod between:
      a blocking position wherein the braking member impinges on the spring-loaded piston rod so as to prevent any translational movement of the spring-loaded piston rod in a distal direction by a bracing effect, wherein the bracing effect is caused by a friction force exerted by the braking member onto the spring-loaded piston rod; and
      a releasing position wherein the braking member disengages from the spring-loaded piston rod so as to allow the spring-loaded piston rod to move towards the distal operative position under a spring force.

2. The injection device of claim 1, wherein the selective blocking mechanism further comprises:
   a lever pivotably mounted on the body about a pivot axis orthogonal to the spring axis, comprising an actuation zone at a first distance from the pivot axis; and
   a connecting rod including a first end coupled to the lever by a second pivot axis opposite the actuating zone relative to the pivot axis, at a second distance from the pivot axis, and a second end coupled to the braking member,
   wherein the lever is pivotable between a rest position wherein the connecting rod constrains the braking member in the blocking position and an actuating position, and
   wherein the connecting rod releases the braking member to the releasing position.

3. The injection device of claim 2, wherein the lever is coupled to the spring-loaded piston rod such that the spring force urges the lever to the rest position.

4. The injection device of claim 2, wherein the first distance is greater than the second distance.

5. The injection device of claim 2, wherein the selective blocking mechanism further comprises a spring member configured to exert a spring force on the braking member so as to constrain the braking member in the blocking position.

6. The injection device of claim 5, wherein the spring member is connected to the body and to the connecting rod or connected to the body and to the braking member.

7. The injection device of claim 1, wherein the braking member comprises an actuation zone configured for moving the braking member from the blocking position to the releasing position, and wherein the selective blocking mechanism further comprises a spring member that urges the braking member to the blocking position.

8. The injection device of claim 7, wherein the spring member is arranged around the spring-loaded piston rod directly in contact with the braking member.

9. The injection device of claim 1, wherein the braking member is a plate provided with a through hole and the spring-loaded piston rod extends through the through hole, an inner surface of the through hole being configured to impinge on the spring-loaded piston rod when the plate is in the blocking position.

10. The injection device of claim 9, wherein the through hole has a dimension greater than the spring-loaded piston rod, the dimension being configured such that when the braking member is tilted in the blocking position, at least a part of the circumference of the through hole contacts an outer wall of the spring-loaded piston rod.

11. The injection device of claim 9, wherein in the releasing position the plate is orthogonal to the spring axis.

12. The injection device of claim 1, wherein the body comprises a container holder system configured to receive at least a portion of the medical container and to hold the medical container aligned with a movement direction along the spring axis of the spring-loaded piston rod so that when moving from the proximal rest position to the distal operative position, the spring-loaded piston rod engages the stopper of the medical container and pushes the stopper in the medical container to inject the composition.

13. The injection device of claim 12, wherein the container holder system comprises:
   an opening provided in a distal wall of the body that leads to a housing adapted to receive at least a portion of the medical container in a position aligned with the movement direction of the spring-loaded piston rod;
   a slot provided in an outer wall of the body that leads to the housing; and
   an insert adapted to be inserted in the slot to contact the medical container and to maintain the medical container in a fixed position in the housing.

14. The injection device of claim 12, wherein the container holder system comprises:
   a slot provided in an outer wall of the body that leads to a housing, configured to receive at least a portion of the medical container and to maintain the medical container in a fixed position aligned with the movement direction of the spring-loaded piston rod; and a through groove provided in a distal wall of the body, continuous with the slot and extending in the distal wall from the slot, the groove being configured to guide the medical container inserted via the slot to the housing.

15. The injection device of claim 1, wherein the injection device is configured to be handheld.

16. The injection device of claim 4, wherein the first distance is at least twice greater than the second distance.

17. An injection device for injecting a composition contained in a medical container comprising:
   a body configured to receive the medical container in a fixed position relative to the body;
   a spring-loaded piston rod translationally movable inside the body along a spring axis, between a proximal rest position and a distal operative position wherein the spring-loaded piston rod engages a stopper of the medical container; and
   a selective blocking mechanism comprising a braking member selectively tiltable relative to the spring-loaded piston rod between:
      a blocking position wherein the braking member impinges on the spring-loaded piston rod so as to prevent any translational movement of the spring-loaded piston rod in a distal direction by a bracing effect; and
      a releasing position wherein the braking member disengages from the spring-loaded piston rod so as to allow the spring-loaded piston rod to move towards the distal operative position under a spring force,
   wherein the braking member comprises an actuation zone configured for moving the braking member from the blocking position to the releasing position,
   wherein the selective blocking mechanism further comprises a spring member that urges the braking member to the blocking position, and
   wherein the spring member is arranged around the spring-loaded piston rod directly in contact with the braking member.

18. An injection device for injecting a composition contained in a medical container comprising:
   a body configured to receive the medical container in a fixed position relative to the body;
   a spring-loaded piston rod translationally movable inside the body along a spring axis, between a proximal rest position and a distal operative position wherein the spring-loaded piston rod engages a stopper of the medical container; and
   a selective blocking mechanism comprising a braking member selectively tiltable relative to the spring-loaded piston rod between:
      a blocking position wherein the braking member impinges on the spring-loaded piston rod so as to prevent any translational movement of the spring-loaded piston rod in a distal direction by a bracing effect; and
      a releasing position wherein the braking member disengages from the spring-loaded piston rod so as to allow the spring-loaded piston rod to move towards the distal operative position under a spring force,
   wherein the body comprises a container holder system configured to receive at least a portion of the medical container and to hold the medical container aligned with a movement direction along the spring axis of the spring-loaded piston rod so that when moving from the proximal rest position to the distal operative position, the spring-loaded piston rod engages the stopper of the medical container and pushes the stopper in the medical container to inject the composition, and
   wherein the container holder system comprises:
      an opening provided in a distal wall of the body that leads to a housing adapted to receive at least a portion of the medical container in a position aligned with the movement direction of the spring-loaded piston rod;
      a slot provided in an outer wall of the body that leads to the housing; and
      an insert adapted to be inserted in the slot to contact the medical container and to maintain the medical container in a fixed position in the housing.

\* \* \* \* \*